(12) United States Patent
Van Assche et al.

(10) Patent No.: US 9,141,576 B2
(45) Date of Patent: *Sep. 22, 2015

(54) INTER-CHIP COMMUNICATIONS FOR IMPLANTABLE STIMULATING DEVICES

(71) Applicant: Cochlear Limited, Macquarie University, NSW (AU)

(72) Inventors: Tom Van Assche, Brussegem (BE); Mark Janssens, Leuven (BE); Geert Carron, Wilsele (BE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/964,669

(22) Filed: Aug. 12, 2013

(65) Prior Publication Data

US 2014/0047154 A1 Feb. 13, 2014

Related U.S. Application Data

(63) Continuation of application No. 13/090,833, filed on Apr. 20, 2011, now Pat. No. 8,509,908.

(51) Int. Cl.
| | |
|---|---|
| *A61N 1/36* | (2006.01) |
| *G06F 13/40* | (2006.01) |
| *B41J 3/44* | (2006.01) |
| *A61N 1/372* | (2006.01) |
| *B41J 2/175* | (2006.01) |
| *B41J 3/413* | (2006.01) |

(52) U.S. Cl.
CPC ........ *G06F 13/4027* (2013.01); *A61N 1/37211* (2013.01); *B41J 3/445* (2013.01); *B41J 2/17503* (2013.01); *B41J 3/413* (2013.01)

(58) Field of Classification Search
CPC . A61N 1/08; A61N 1/36125; A61N 1/37211; A61N 1/37217
See application file for complete search history.

(56) References Cited

U.S. PATENT DOCUMENTS

| | | |
|---|---|---|
| 5,266,919 A | 11/1993 | Cook et al. |
| 5,268,937 A | 12/1993 | Marbot |
| 5,625,563 A | 4/1997 | Rostoker et al. |

(Continued)

FOREIGN PATENT DOCUMENTS

| | | |
|---|---|---|
| EP | 1702648 A2 | 9/2006 |
| WO | 2011/011327 | 1/2011 |

OTHER PUBLICATIONS

International Search Report & Written Opinion for International Application No. PCT/IB2012/051847 mailed Nov. 23, 2012 (10 pages).

(Continued)

*Primary Examiner* — Brian T Gedeon

(57) ABSTRACT

A device including a first integrated circuit (IC), a second IC configured to provide instructions to the first IC based on received data, wherein the first IC is a high-voltage IC and the second IC is a low-voltage IC, and a communication interface between the first and second ICs including a data bus of parallel data lines. The second IC is configured to select, based on the received data, one of a plurality of different communication modes for providing the instructions to the first IC via the communication interface, wherein each mode is defined by a quantity of address data and a quantity of configuration data used to provide the instructions to the first IC.

28 Claims, 11 Drawing Sheets

(56) References Cited

U.S. PATENT DOCUMENTS

| | | |
|---|---|---|
| 5,717,818 A | 2/1998 | Nejime et al. |
| 6,263,385 B1 | 7/2001 | Gulick et al. |
| 6,330,339 B1 | 12/2001 | Ishige et al. |
| 6,496,729 B2 | 12/2002 | Thompson |
| 6,845,461 B1 | 1/2005 | Kim |
| 6,895,518 B2 | 5/2005 | Wingen |
| 7,176,724 B1 | 2/2007 | Delson |
| 7,180,949 B2 | 2/2007 | Kleveland et al. |
| 7,289,852 B2 | 10/2007 | Helfinstine et al. |
| 8,089,787 B2 | 1/2012 | Melse |
| 2003/0056137 A1 | 3/2003 | Huelskamp |
| 2003/0114897 A1 | 6/2003 | Von Arx et al. |
| 2004/0122490 A1 | 6/2004 | Reinke et al. |
| 2007/0027485 A1 | 2/2007 | Kallmyer et al. |
| 2007/0123946 A1 | 5/2007 | Masoud |
| 2007/0185550 A1 | 8/2007 | Vallapureddy et al. |
| 2008/0319497 A1 | 12/2008 | Griffith et al. |
| 2010/0114248 A1 | 5/2010 | Donofrio et al. |
| 2012/0095519 A1 | 4/2012 | Parramon et al. |

OTHER PUBLICATIONS

Extended European Search Report in counterpart European Application No. 12774594.1, mailed May 5, 2014, 6 pages.

Examination Report in European Application No. 12774594.1, mailed Apr. 1, 2015, 3 pages.

English language translation of Search Report in counterpart Chinese Application No. 201280030049.0, dated Jun. 18, 2015, 2 pages.

Chinese Office Action (with English language translation) in counterpart Chinese Application No. 201280030049.0, dated Jun. 30, 2015, 9 pages.

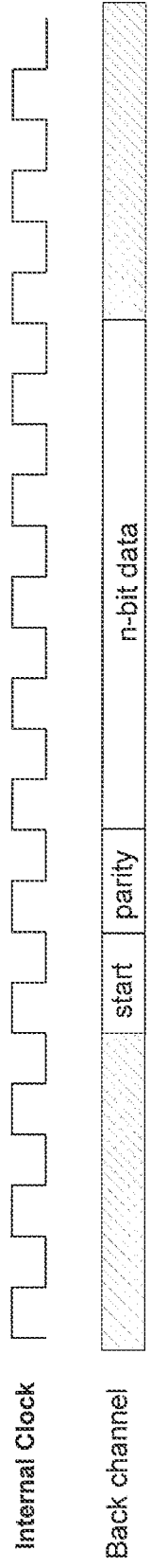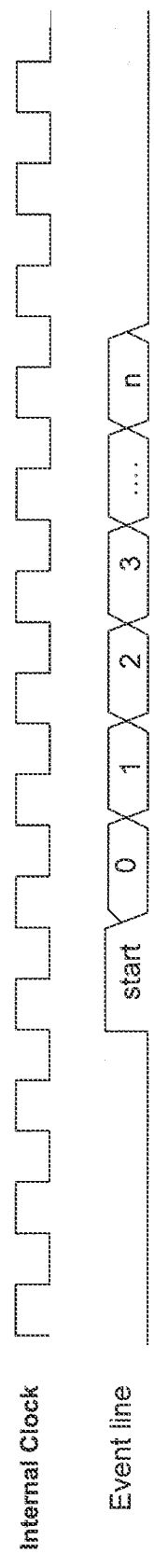

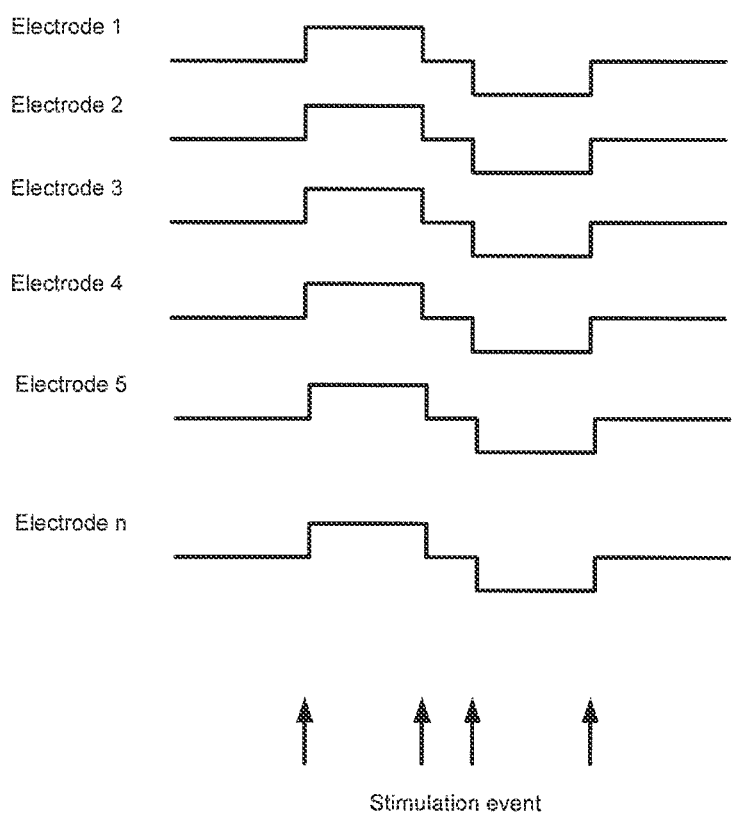

FIG. 10

| Electrode 1: configuration data | Electrode 2: configuration data | Electrode 3: configuration data | ... | Electrode n: configuration data |

FIG. 11

| Electrode address (0) | configuration data (0) | Electrode address (1) | configuration data (1) | Electrode address (2) | configuration data (2) | ... | Electrode address (n) | configuration data (n) |

FIG. 12

| BITMAP | configuration data (0) | configuration data (1) | configuration data (2) | configuration data (3) | configuration data (4) | ... | configuration data (n) |

FIG. 13

| configuration data |

| | | cycle 1 | cycle 2 |
|---|---|---|---|
| 7 | start cycle | | |
| 6 | data ch.: 1 | | |
| 5 | Read/nWrite: 0 | | |
| 4 | CRC transfer | 10-bit address | 8-bit data |
| 3 | unused | | |
| 2 | | | |
| 1 | | | |
| 0 | | | |

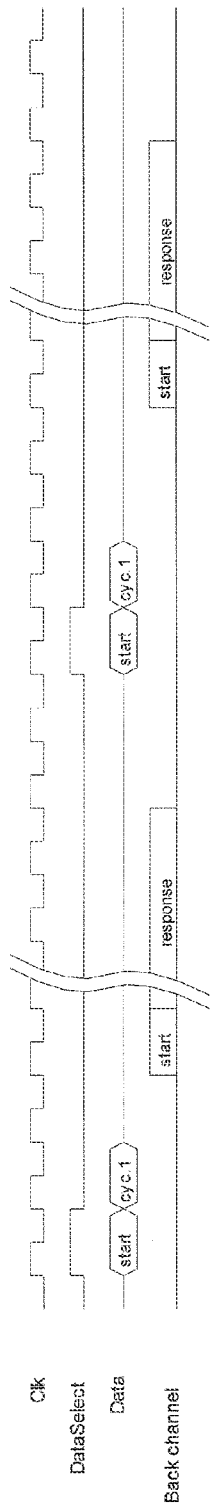

INTER-CHIP COMMUNICATIONS FOR IMPLANTABLE STIMULATING DEVICES

CROSS-REFERENCE TO RELATED APPLICATIONS

This application is a continuation of U.S. patent application Ser. No. 13/090,833, entitled "INTER-CHIP COMMUNICATIONS FOR IMPLANTABLE STIMULATING DEVICES", filed on Apr. 20, 2011, the entire contents and disclosures of which are hereby incorporated by reference herein.

BACKGROUND

1. Field of the Invention

The present invention relates generally to implantable stimulating devices, and more particularly, to inter-chip communications for implantable stimulating devices.

2. Related Art

Implantable stimulating devices having one or more implantable components are used in various applications to provide electrical stimulation to recipients. Exemplary implantable stimulating devices include hearing prostheses, cardiac devices, incontinence devices, and other therapeutic and diagnostic devices.

Power consumption is a critical design consideration for implantable stimulating devices. In some implantable stimulating devices, an external device is used to provide power to the implantable stimulating device through the skin via a transcutaneous inductive link, or another arrangement. This link may be operated to continuously supply power to the implantable stimulating device, as in many cochlear implants, for example, or may be operated periodically, so as to provide power to an implantable power storage device (or "power supply"). An alternative for some implantable stimulating devices is to use an implantable power supply that may be replaced through minor surgery. In each of these alternatives, however, the power available within the implantable stimulating device is very limited.

SUMMARY

In one aspect of the present invention, a device is provided that comprises a first integrated circuit (IC), a second IC configured to provide instructions to the first IC based on received data, wherein the first IC is a high-voltage IC and the second IC is a low-voltage IC, and a communication interface between the first and second ICs including a data bus of parallel data lines. The second IC is configured to select, based on the received data, one of a plurality of different communication modes for providing the instructions to the first IC via the communication interface, wherein each mode is defined by a quantity of address data and a quantity of configuration data used to provide the instructions to the first IC.

In another aspect of the present invention, a stimulating medical device is provided. The stimulating medical device comprises a stimulator integrated circuit (IC) configured to output electrical stimulation via a plurality of electrodes in response to stimulation instructions, a processor IC configured to provide the stimulation instructions to the simulator IC based on received data, and a communication interface between the stimulator and processor ICs including a data bus of parallel data lines, wherein the processor IC is configured to select, based on the received data, one of a plurality of different communication modes for providing the instructions to the stimulator IC via the communication interface, wherein each mode is defined by a quantity of address data and a quantity of configuration data used to provide the instructions to the stimulator IC.

In yet another aspect of the present invention, a method for operating a medical device is provided. The device includes a stimulator integrated circuit (IC) configured to output electrical stimulation via a plurality of electrodes in response to stimulation instructions, a processor IC configured to provide the stimulation instructions to the stimulator IC via a communication interface having a data bus of parallel data lines, and a plurality of addressable components. The method comprises selecting one of a plurality of communication modes based on data received by the processor IC, wherein each mode is defined by a quantity of address data and a quantity of configuration data used to provide the instructions to the stimulator IC, and providing the instructions, based on the received data, to the stimulator IC via the communication interface using the selected communication mode.

BRIEF DESCRIPTION OF THE DRAWINGS

Illustrative embodiments of the present invention will now be described with reference to the accompanying drawings, in which:

FIG. 7 is a timing diagram illustrating the timing of data provided on a back channel of the communication interface relative to an internal clock signal of a stimulator integrated circuit (IC) in accordance with embodiments of the present invention;

FIG. 8 is a timing diagram illustrating the timing of data provided on an event line relative to an internal clock signal of the stimulator IC in accordance with embodiments of the present invention;

FIG. 9 is a timing diagram showing the timing of stimulation events in accordance with embodiments of the present invention;

FIG. 10 is an illustration of the data format used for a first mode of reconfiguring the electrodes in accordance with embodiments of the present invention;

FIG. 11 is an illustration of the data format used for a second mode of reconfiguring the electrodes in accordance with embodiments of the present invention;

FIG. 12 is an illustration of the data format used for a third mode of reconfiguring the electrodes in accordance with embodiments of the present invention;

FIG. 13 is an illustration of the data format used for a fourth mode of reconfiguring the electrodes in accordance with embodiments of the present invention;

FIG. 16A illustrates a read message frame for reading data from the stimulator IC in accordance with embodiments of the present invention; and FIG. 16B is a timing diagram for several signals during a read operation from the stimulator IC in accordance with embodiments of the present invention.

DETAILED DESCRIPTION

Figure 1:
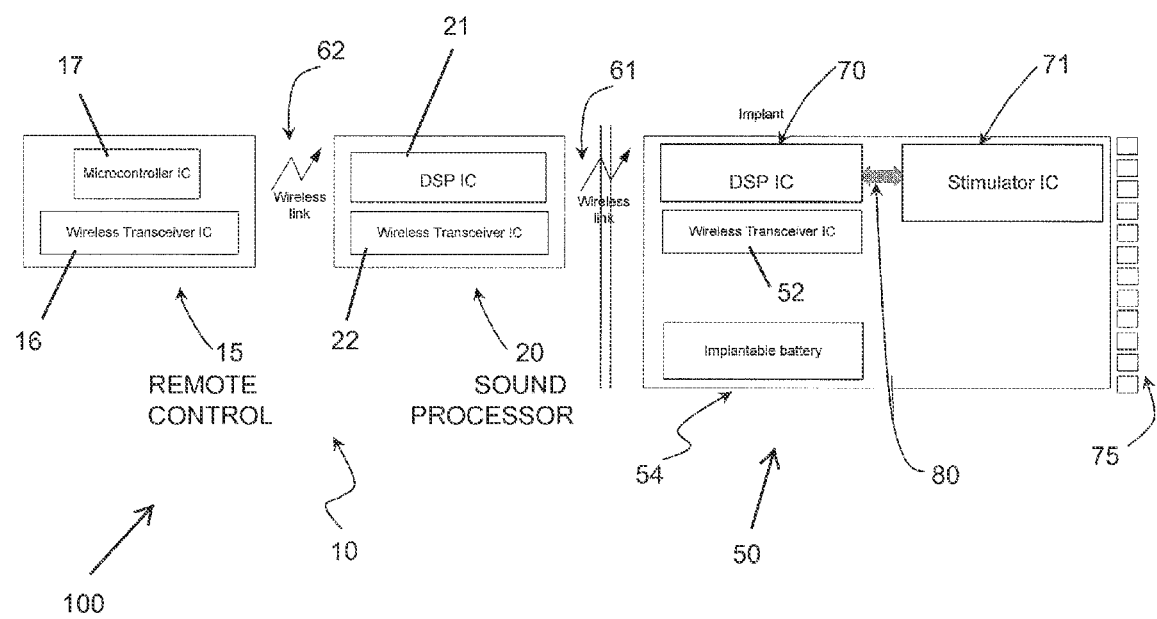
FIG. 1 is a structural block diagram of an implantable hearing prosthesis having a two-chip implementation in accordance with embodiments of the present invention.

Aspects of the present invention may be implemented in devices having two or more integrated circuits (ICs), where one is a mixed signal IC and the other is a digital IC. Embodiments of the present invention may be applied in devices such as medical devices, such as stimulating medical devices including a high-voltage stimulator IC and a low-voltage digital processor IC in communication with a plurality of addressable components, such as electrodes. More particularly, embodiments of the invention may be implemented in a cochlear implant having a low-voltage digital IC and a high-power, mixed signal stimulator IC configured to output electrical stimulation via a plurality of electrodes of an electrode array.

One type of implantable stimulating device is an implantable hearing prosthesis. Conventionally, an implantable hearing prosthesis may be implementing using a single chip, such that all the processing within the hearing prosthesis is performed on a single IC. As a result of technological advances in IC fabrication technology leading to further miniaturization ICs, there is a trend towards incorporating increasing amounts of digital logic on the IC of the hearing prosthesis to increase the processing power of the IC. Increasing the processing power of the IC is expected to provide improved performance and functionality of the hearing prosthesis.

Implantable stimulating devices, such as the implantable hearing prosthesis described above, often provide electrical stimulation to a recipient via one or more electrodes. An interface between the IC and the electrodes often requires the use of high-voltage transistors, typically around 6-20V. Such high-voltage technology extensions are generally designed for older, larger-dimension IC technologies. Accordingly, as IC dimensions are reduced, it will become increasingly more difficult to provide a single chip for an implantable hearing prosthesis, as newer fabrication techniques will be unable to provide high-voltage transistors appropriate for stimulation. In certain embodiments of the present invention, a prosthesis may instead use two chips: one low-voltage chip, such as a digital chip, for processing and one high-voltage chip for providing high-voltage transistors. In certain embodiments, a prosthesis using two such chips may also include an interface for communications between the two chips.

In certain embodiments, a low-voltage chip (which may be referred to herein as a low-voltage IC) is an IC in which the maximum voltage utilized by the IC is significantly lower than the maximum voltage utilized by a high-voltage chip (which may be referred to herein as a high-voltage IC). For example, in certain embodiments, the maximum voltage utilized by the high-voltage IC may be five to ten times greater than the maximum voltage utilized by the low-voltage IC. In some embodiments, the highest voltage utilized by a high-voltage stimulator IC is at least twice as high as the highest voltage utilized by a low-voltage processor IC. Additionally, this difference may increase as technology advances. In some embodiments, a low-voltage chip is an IC in which the maximum voltage utilized is between 1.8 volts and 3.3 volts. In certain embodiments, the low-voltage IC may utilize a maximum voltage of between 1.4 and 1.8 volts for communication with a high-voltage chip, and may utilize a maximum voltage of up to 3.3 volts at an interface with another type of device, such as a memory device. In certain embodiments, a low-voltage IC is an IC in which the maximum voltage utilized by the IC is below 5 volts. In some embodiments, a high-voltage IC is an IC in which the maximum voltage utilized by the IC is at least 5 volts. In certain embodiments, a high-voltage IC may utilize a maximum voltage of between about 6 and 20 volts.

In embodiments of the present invention having a high-voltage IC and a low-voltage IC, it may be beneficial to maximize the number of functions implemented on the low-voltage IC and minimize the number of functions implemented on the high-voltage IC to reduce the power consumption of the device. In certain embodiments, a device having a high-voltage, mixed signal stimulator IC and a low-voltage, digital processor IC, it may be beneficial to perform little other than the generation of stimulation signals on the stimulator IC while performing other functions on the processor IC or in another part of the device. In certain embodiments, such a division of functionalities may provide a reduction in the power consumption of the device, as few functionalities are implemented on the high-voltage stimulator IC and are instead implemented on the low-voltage digital IC or in by another component of the device. In some embodiments, such a division of functionalities may also provide a reduction in the size of the device, as the functionalities may be implemented in much smaller dimensions in newer digital technologies than in analog technologies of a mixed signal IC such as the stimulator IC. In certain embodiments, the mixed signal stimulator IC may be more than 50% analog. In such embodiments, the digital circuitry of the mixed signal stimulator IC may be used only to interface with the processor IC.

Inter-chip signalling is much less efficient in multiple-chip implementations than intra-chip signalling. Utilizing the same processes and communications protocols between two chips that were previously used within a single chip will lead to very significant increases in power consumption.

Aspects of the present invention will be described with reference to a particular illustrative example, which is a device intended for use in a cochlear implant. However, it will be appreciated that embodiments of the present invention is applicable wherever two ICs may be used to communicate stimulation data within an implantable stimulating device. For example, embodiments of the present invention may be implemented in an implantable hearing prosthesis, such as a cochlear implant, brain stem implant, hybrid electrical/acoustic system, a hearing aid system, or any other suitable hearing prosthesis. As used herein, "implantable" devices include both totally implantable devices and partially implantable devices that have at least one implantable component. Certain embodiments may be implemented in a totally implantable system or to a partially implantable system. Embodiments of the present invention may also be implemented in any other implantable device providing electrical stimulation, such as, for example, cardiac devices, incontinence devices, and other muscle and neural stimulators.

Existing implantable hearing prostheses are typically implemented in a single chip. As noted above, due to the miniaturization of IC technology, there is a trend towards incorporating more digital logic into implantable stimulating devices in order to provide improved functionality and performance. However, as noted above, IC miniaturization may make it difficult to provide a high-voltage interface between the IC and the electrodes of the stimulating device. Accordingly, certain embodiments of the present invention are directed to implantable stimulating devices that utilize two chips: one chip fabricated using deep-submicron technologies, and one chip providing high-voltage transistors to provide an interface with the electrodes.

FIG. 1 is a structural block diagram of an implantable hearing prosthesis 100 having a two-chip implementation in accordance with embodiments of the present invention. Hearing prosthesis 100 includes an external system 10 and an implantable system 50. Implantable system 50 is adapted to provide the required therapy, in this case electrical stimulation, which may provide a hearing precept to a hearing impaired recipient in certain embodiments. External system 10 includes an external sound processor 20 that incorporates a signal processor IC 21 and a wireless transceiver IC 22. Sound processor 20 operates to capture an audio signal received from a microphone (not shown), condition and encode the captured audio signal in signal processor IC 21, and transfer the output via wireless transceiver 22 to the implanted system 50, using a wireless link 61. External system 10 also includes a wireless remote control 15, which in this implementation communicates via a wireless link 62 with the sound processor 20, and one or more microphones or other sound pickup devices (not illustrated). Remote control 15 includes a microcontroller IC 17, and a wireless transceiver IC 16. External system 10 would typically also provide power, via an inductive link (e.g., wireless link 61), to charge implantable battery 54 of implantable system 50. In some implementations, the externally supplied power may be provided to implantable system 50 continuously. In other implementations, the externally supplied power may be provided periodically.

Implantable system 50 includes a digital signal processor (DSP) IC 70, a wireless transceiver IC 52 (for communicating with external system 10), a stimulator IC 71, a communication interface 80, and an implantable battery 54. The function of the external and implantable systems may be entirely conventional, and for details of the nature of therapy, and details of construction of cochlear implants, the reader is referred to the currently commercially available products, for example the products of Cochlear Limited, and to the numerous references in the field. Specific therapies will not be described herein in detail, rather embodiments will be described herein in relation to the operation of a communication interface between multiple ICs in any one of various implantable stimulating devices, as discussed above. Additionally, embodiments of the present invention are not limited to any particular division in processing between the stimulator IC and the DSP IC. Rather, the implementation described herein is merely one possibility.

In the embodiment illustrated in FIG. 1, the two-chip implementation includes digital signal processing (DSP) IC 70, which would be typically implemented in a deep submicron technology, and a stimulator IC 71, which provides an interface to electrodes 75 (or other components in other implementations). Stimulator IC 71 may be implemented such that it uses only analog signals, or both digital and analog signals. DSP IC 70 and stimulator IC 71 communicate via an inter-chip communication interface 80. Communication interface 80 (which may be referred to as an "inter-chip" communication interface or an "off-chip" communication interface) is preferably a high-speed interface that provides protocol-transparent communications between the two ICs. The rate of data communication (i.e., the bandwidth) over communication interface 80 is preferably flexible and capable of achieving high rates of data communication. Communication interface 80 also preferably provides predictable latency, a parallel bus for communicating data, and low power consumption. Finally, communication interface 80 is preferably be very robust.

In the embodiment illustrated in FIG. 1, audio data is processed on the implanted DSP IC 70, so as to produce stimulation instructions, while the actual stimulation is carried out by stimulator IC 71, which includes high-voltage transistors through which stimulator IC 71 is able to drive the electrodes 75. Therefore, real-time isochronous stimulation instructions are transferred over communication interface 80. DSP IC 70 determines the exact timing of stimulation to be applied by the device, while stimulator IC 71 contains the appropriate circuitry to create such timing (e.g., a crystal oscillator). DSP IC 70 can run on a low-power clock signal (e.g., a clock signal generated by a free running oscillator or FRO).

In general, communication between ICs consumes more power than intra-chip communication. Therefore, aspects of the present invention are directed to lowering the amount of power consumed by a communication interface between ICs.

Figure 4:
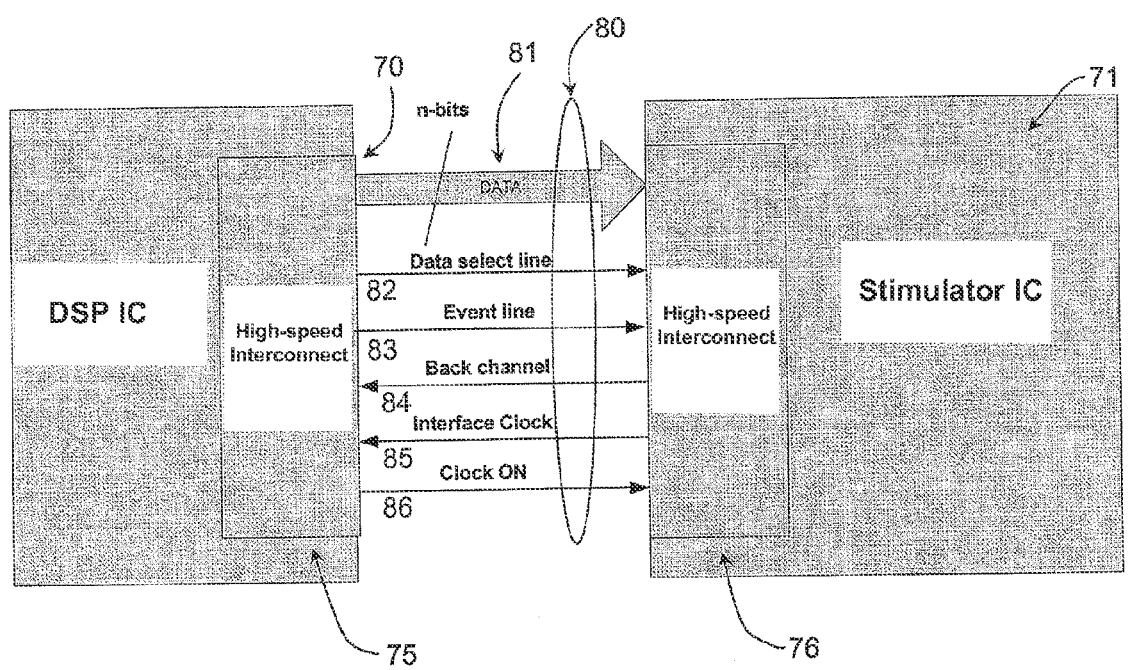
FIG. 4 is a structural block diagram of one physical implementation of a communication interface between ICs in accordance with embodiments of the present invention.

FIG. 4 is a structural block diagram of one physical implementation of a communication interface between ICs in accordance with embodiments of the present invention. Communication interface 80 connects DSP IC 70 and stimulator IC 71, and includes several lines illustrated in FIG. 4. Communication interface 80 is a synchronous bi-directional interface between high speed interconnects 75 and 76 of DSP IC 70 and stimulator IC 71, respectively. Communication interface 80 includes a data select line 82, an n-bit inter-chip bus 81 (which may be referred to herein as a data bus 81), an event line 83, a back channel 84, an interface clock line 85, and an interface clock enable line 86. Data bus 81 consists of an n-bit parallel bus and therefore a large amount of data can be moved over this interface. Data bus 81 and select line 82 form the physical forward data connection (which may be referred to herein as the "forward data channel"), and event line 83 is the physical event connection. In the embodiment shown in FIG. 4, back channel 84 provides the physical return connection and is a single line that is used by DSP IC 70 to read values from stimulator IC 71.

Figure 5:
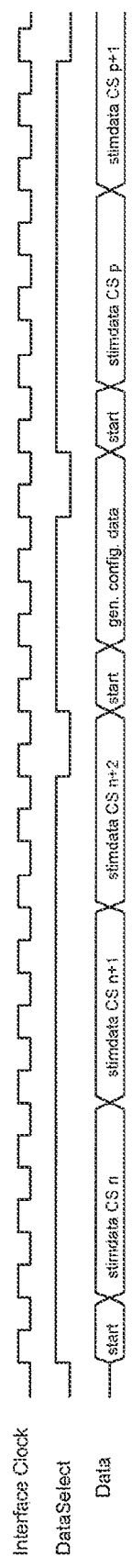
FIG. 5 is a timing diagram illustrating the timing of signals provided over the communication interface in accordance with embodiments of the present invention.

FIG. 5 is a timing diagram illustrating timing of signals provided over communication interface 80 in accordance with embodiments of the present invention. The forward channel transfers data synchronously from DSP IC 70 to stimulator IC 71. FIG. 5 shows the timing of signals on data bus 81 (labelled "Data") and data select line 82 (labelled "DataSelect") relative to an interface clock signal provided on interface clock line 85. The forward channel provides both stimulation instructions and general configuration data from DSP IC 70 to stimulator IC 71.

Figure 6:
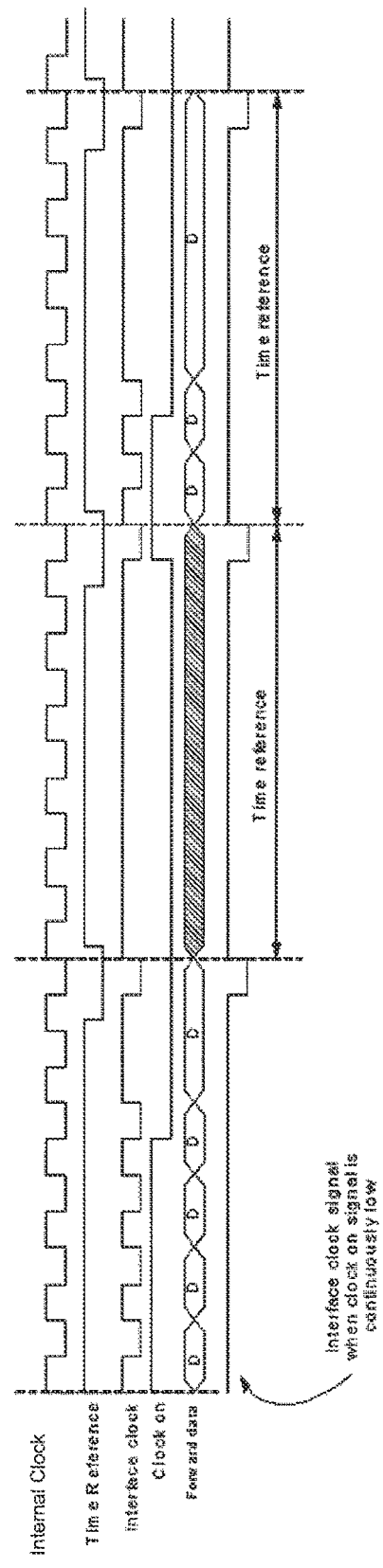
FIG. 6 is a timing diagram illustrating the timing of several signals during a data transfer using the communication interface in accordance with embodiments of the present invention.

FIG. 6 is a timing diagram illustrating the timing of several signals during a data transfer using communication interface 80 in accordance with embodiments of the present invention. FIG. 6 shows the timing of signals including an internal clock of the stimulation IC, a time reference signal, an interface clock signal, a signal provided on the clock enable line 86 (labelled "Clock on"), and signals on data bus 81 (labelled "Forward data"). Each transfer over data bus 81 starts with the data select line going high when the first byte of data appears on the interface, as indicated in FIG. 5. The data select line remains high until the beginning of the last transfer cycle of the last byte transferred. During this final transfer cycle, the data select line is already low such that it is ready for a possible new transfer at the first cycle after the current one finishes.

For back channel 84, one uni-directional wire is provided to make the complete interface full duplex. This allows DSP IC 70 to transfer new stimulation instructions while data are being received via back channel 84. Stimulator IC 71 uses back channel 84 to provide a response when data is requested on the forward data channel. FIG. 7 is a timing diagram illustrating the timing of data provided on back channel 84 relative to an internal clock signal of stimulator IC 71. As illustrated in FIG. 7, data provided over back channel 84 is formatted into a start cycle, a parity cycle and an n-bit data cycle. The data provided over back channel 84 is always over the same number of clock cycles. In an alternative implementation, back channel 84 could be a multi-channel bus. A tri-state interface is not preferred, because this increases the complexity due to direction switching, which itself also increases the power consumption due to the possibility of short-circuit currents.

Event line 83 (which may be referred to herein as an "event indication line") is used to precisely time stimulation events for the stimulator IC. Thus, DSP IC 70 activates this line on event time grids. Event notifications are very time-critical and generally take priority over all other communication in certain embodiments. To reduce the complexity of this communication, a separate line may be used for event notifications. FIG. 8 is a timing diagram illustrating the timing of data provided on event line 83 relative to an internal clock signal of stimulator IC 71 in accordance with embodiments of the present invention. In the embodiment illustrated in FIG. 8, data provided over event line 83 is formatted into a start cycle and a parity cycle followed by n 1-bit cycles to indicate and define an event.

Because communication between separate ICs requires more power than communication within a single IC, in certain embodiments it is preferable that the bus is low-power by concept and design. The power consumption of a digital circuit depends on the switching activity of its internal nodes. In this context, an activity factor $\alpha$ is defined as the expected number of transitions per data cycle. If this is coupled to an average data-rate, f, which is normally equal to the clock frequency in a synchronous system, then the effective frequency of nodal charging/discharging is given by the product of the activity factor and the data rate, which is $\alpha*f$. As such, the following formula may be provided for the average power consumption of a complementary metal-oxide-semiconductor (CMOS) digital circuit:

$$Pdyn = \alpha * f * C * VDD^2$$

In the above formula, VDD represents the supply voltage and C the total switching capacity of the circuit, which is related to the area of the circuitry (and to the complexity of the circuitry).

The communication interface 80 is a synchronous interface in which stimulator IC 71, in the embodiment illustrated in FIG. 1, generates the interface clock signal. Stimulator IC 71 preferably generates the interface clock signal because it also generates the system time reference, and because it is the stimulation that is most carefully timed in certain embodiments. In some embodiments, both ICs 70 and 71 preferably run on a common time reference (or reference clock). The interface clock signal illustrated in FIG. 6 can be used both as a reference clock for DSP IC 70 and as an interface clock. However, in order to provide the desired high bandwidth (i.e., data rate) interface when large volumes of data are required to be transferred, the clock frequency during data communication should be much higher than the clock frequency required for generating a reliable reference clock. Accordingly, interface clock line 85, in accordance with embodiments of the present invention, is operated in two modes: one during data communication, when a relatively fast (i.e., high frequency) clock signal is provided on interface clock line 85; and a second mode during times when data is not being communicated and a slower (i.e., lower frequency) reference clock signal is provided on clock line 85 for DSP IC 70. While generated by stimulator IC 71, the clock signal is controlled by a clock enable signal generated by DSP IC 70 and provided over clock ON line 86.

The first and second modes described above are illustrated in the timing diagram of FIG. 6. The time reference (i.e., reference clock) can have a reduced frequency, for instance 1 MHz, when data is not being communicated. To communicate with stimulation IC 71, DSP IC 70 asserts the 'clock ON' signal over clock ON line 86. In response to the clock ON signal, stimulator IC 71 generates a faster clock signal, for example 10 MHz, until the clock ON signal is de-asserted. By controlling clock ON line 86, DSP IC 70 can cause communication interface 80 to operate at a much higher clock speed, and hence a much higher bandwidth for data transfer, than during the slower, reference clock phase.

In certain embodiments, one function of communication interface 80 is transferring stimulation instructions for stimulation electrodes 75. Stimulation instructions are provided prior to each stimulation event, and so stimulation instructions are sent every time the status of one or more electrodes needs to change. As used herein, "stimulation instructions" include configuration data for one or more electrodes. Additionally, in certain embodiments, stimulation instructions may include address information for one or more electrodes and timing information corresponding to the configuration data. As used herein, "configuration data" includes any of the parameters of the electrical stimulation to be delivered at a designated electrode during a stimulation event. In certain embodiments, the configuration data for an electrode includes the magnitude of electrical stimulation for the electrode. In some embodiments, timing information corresponding to the magnitude of stimulation is separate from the configuration data. In other embodiments, the configuration data may include the timing information. In certain embodiments, the configuration data may be equal to, part of, or derived from stimulation data generated by a DSP IC in response to received audio data, as described further below. As used herein, a "stimulation event" refers to a change in the one or more stimulation parameters of one or more electrodes. In the example illustrated in FIG. 9, each of the arrows indicates a stimulation event. At each of the illustrated stimulation events, the magnitude of the electrical stimulation changes for one or more of the electrodes. In certain embodiments, the respective magnitudes at any of one or more of the electrodes may change at a given stimulation event.

FIG. 9 illustrates the timing of stimulation events for one embodiment of the present invention. It will be appreciated that embodiments of the present invention are not limited in application to any particular stimulation pattern. Referring to FIG. 9, for each electrode that is to be stimulated, electrical stimulation of a first magnitude is applied during a first stimulation phase. Then, after a pause, a second electrical stimulation of an equal and opposite magnitude is applied during a second stimulation phase. In embodiments, the second stimulation phase preferably delivers the same amount of charge as the first phase, which is generally achieved by delivering a stimulation of equal but opposite magnitude for current for the same duration as the stimulus applied during the first phase.

In certain embodiments, stimulation instructions may be provided from DSP IC 70 to stimulator IC 71 using one of four different modes. In such embodiments, changes in the stimulation parameters of the electrodes controlled by stimulator IC 71 can be communicated using one of the four different modes. The four modes may be summarized as reconfiguring all of the electrodes, reconfiguring individual electrodes specified by an address, reconfiguring a selected group of electrodes specified by a bitmap, and reconfiguring all electrodes with identical configuration data. Additionally, in certain embodiments, each of the different modes is defined by a quantity of address data and a quantity of configuration data used to provide instructions to the stimulator IC 71. More generally, in certain embodiments, the modes may be used for providing instructions related to one or more addressable components of the device. As used herein, "addressable component" refers to any component of a device that may be specified or otherwise identified by an identifier, such as an address, number, ID, etc., corresponding to that component. In certain embodiments, the addressable components are electrodes of a stimulating medical device, such as a hearing prosthesis.

Each of the modes mentioned above will be discussed in more detail below. In some embodiments, using the different modes may allow the least power intensive mode capable of achieving the required changes to be used. In certain embodiments, this mode selection will improve the efficiency of the use of power by the stimulating device. Generally, the more communication required, the higher the power consumption.

Reconfiguring All the Electrodes

FIG. 10 is an illustration of the data format used for a first mode of reconfiguring the electrodes in accordance with embodiments of the present invention. In the first mode (which may be referred to herein as a "full reconfiguration mode"), DSP IC 70 reconfigures all the electrodes for the stimulation event. This method requires much communication, and thus is beneficial when the configuration data for most or all of electrodes 75 need to be changed simultaneously. As illustrated in FIG. 10, a full set of configuration data is separately provided for each electrode 75. Because configuration data is provided for each electrode in a fixed order, no electrode addresses are provided in this mode. In such embodiments, stimulator IC 71 will know which configuration data to apply to which electrode based on the order in which the configuration data is received.

Addressing Individual Electrodes

FIG. 11 is an illustration of the data format used for a second mode of reconfiguring the electrodes in accordance with embodiments of the present invention. In the second mode (which may be referred to herein as an "individual addressing mode"), the configuration data for a few electrodes is changed for the stimulation event. In this mode, configuration data is provided together with the electrode address (or number) for each of the electrodes being reconfigured. More specifically, for each electrode to be reconfigured, the address of the specific electrode to be reconfigured is provided, followed by the configuration data for the specified electrode. In certain embodiments, the address data for each electrode is greater than one bit. In some embodiments, for example, each electrode has a one-byte electrode address (or ID).

Reconfiguring a Selected Group of Electrodes

FIG. 12 is an illustration of the data format used for a third mode of reconfiguring the electrodes in accordance with embodiments of the present invention. The third mode (which may be referred to herein as a "bitmap addressing mode") may be used when the configuration data for less than all of the electrodes is to be changed for the stimulation event. The electrodes being reconfigured are specified by providing a bitmap to stimulator IC 70 that indicates which electrodes are to be reconfigured. After the bitmap is provided, the new configuration data for each of the specified electrodes is provided. Since the selected electrodes are known from the bitmap, and the order of the data transfer is fixed, the transfer can be done without providing an explicit electrode address for each electrode receiving new configuration data. The third mode is beneficial when the sum of the address bits of the individual electrodes that would be provided in the second mode exceeds the number of bits in the bitmap. In certain embodiments, each electrode is specified by one bit in the bitmap. In such embodiments, the value of a specific bit in the bitmap may indicate whether an electrode corresponding to that bit is to be reconfigured. In some embodiments, a four-byte bitmap having one bit representing each electrode may be used.

Reconfiguring All Electrodes with an Identical Configuration: Broadcast Message

FIG. 13 is an illustration of the data format for used for a fourth mode of reconfiguring the electrodes in accordance with embodiments of the present invention. The fourth mode can be useful when all electrodes are to be reconfigured with the same data. For instance, in certain embodiments, all electrodes are preferably switched to the same state between stimulation pulses. The fourth mode (which may be referred to herein as a "broadcast addressing mode" or "broadcast mode") allows writing one configuration to all of the electrodes. In such embodiments, in response to receiving an amount of configuration data substantially equivalent to an amount configuration data sufficient to reconfigure only one single electrode, one stimulator IC 71 may apply the received configuration data to each of the electrodes.

In certain embodiments, after choosing a mode of reconfiguring the electrodes, a conventional data format may be used. Alternatively, the stimulation data format could be selected to maximise the benefits of implementing embodiments of the present invention.

In certain embodiments, the different modes require different amounts of data, and hence communication bandwidth, to implement.

In some embodiments, the first mode (i.e., the full reconfiguration mode) requires a 1 byte header, and 2 bytes of configuration data for each electrode. Hence, the formula representing the amount of data required for this mode is $1+2*N_{max}$, where $N_{max}$ is the maximum number of electrodes.

In some embodiments, the second mode (i.e., the individual addressing mode) requires a 1 byte header, a 1 byte electrode ID for each electrode and 2 bytes of data for each electrode. The formula representing the amount of data required for this mode is accordingly $1+3*N$.

In some embodiments, the third mode (i.e., the bitmap addressing mode) requires a one byte header (which includes part of the bitmap), a 4 byte bitmap and 2 bytes of data for each electrode, for a total data requirement of $5+2N$, where N is the number of electrodes being reconfigured.

Figure 14:
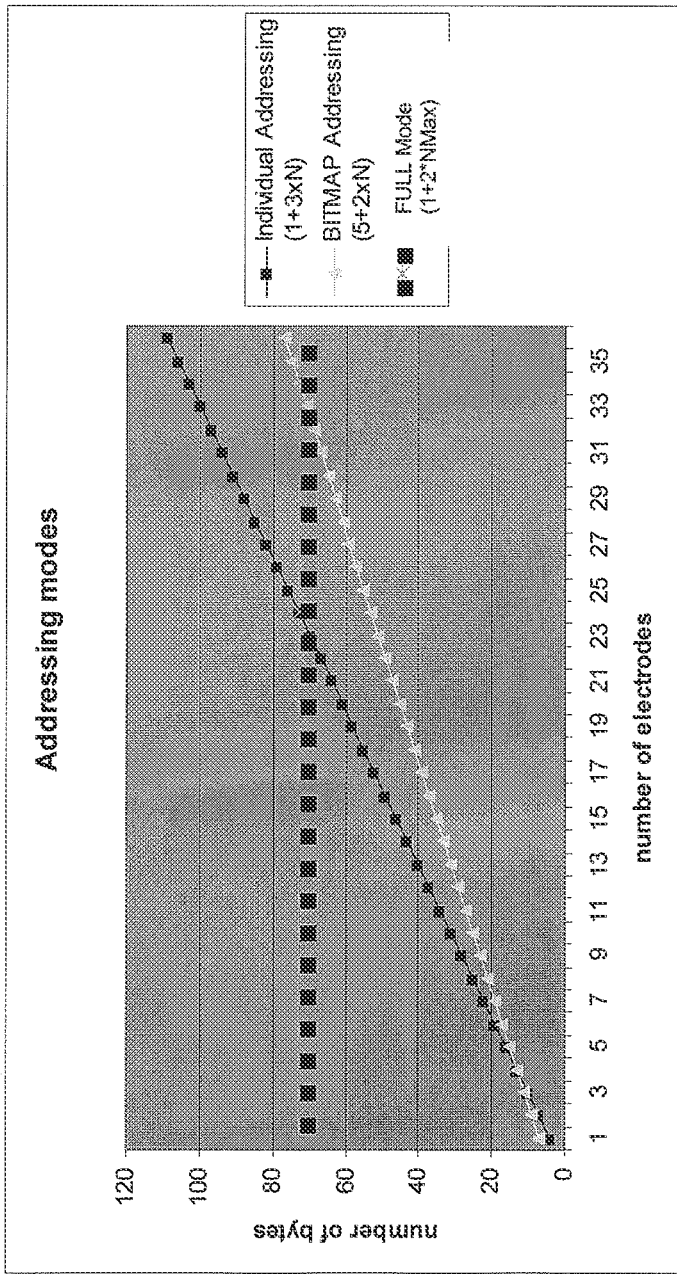
FIG. 14 is a graph illustrating data requirements for different modes of operating the communication interface in accordance with embodiments of the present invention.

FIG. 14 is a graph illustrating data requirements for different modes of operating communication interface 80 in accordance with embodiments of the present invention. It can be seen that when only few electrodes are reconfigured, individual addressing and bitmap addressing modes can be much more efficient.

For example, consider the following example in which the maximum number of electrodes is 36. The following table shows the data requirement for three different modes based on how many electrode configurations are changing.

| Electrode nr. | Individual Addressing (1 + 3 × N) | BITMAP Addressing (5 + 2 × N) | FULL Reconfiguration (1 + 2 * Nmax) |
|---|---|---|---|
| 1 | 4 | 7 | 73 |
| 2 | 7 | 9 | 73 |
| 3 | 10 | 11 | 73 |
| 4 | 13 | 13 | 73 |
| 5 | 16 | 15 | 73 |
| 6 | 19 | 17 | 73 |
| 7 | 22 | 19 | 73 |
| 8 | 25 | 21 | 73 |
| 9 | 28 | 23 | 73 |
| 10 | 31 | 25 | 73 |
| 11 | 34 | 27 | 73 |
| 12 | 37 | 29 | 73 |
| 13 | 40 | 31 | 73 |
| 14 | 43 | 33 | 73 |
| 15 | 46 | 35 | 73 |
| 16 | 49 | 37 | 73 |
| 17 | 52 | 39 | 73 |
| 18 | 55 | 41 | 73 |
| 19 | 58 | 43 | 73 |
| 20 | 61 | 45 | 73 |
| 21 | 64 | 47 | 73 |
| 22 | 67 | 49 | 73 |
| 23 | 70 | 51 | 73 |
| 24 | 73 | 53 | 73 |
| 25 | 76 | 55 | 73 |
| 26 | 79 | 57 | 73 |
| 27 | 82 | 59 | 73 |
| 28 | 85 | 61 | 73 |
| 29 | 88 | 63 | 73 |
| 30 | 91 | 65 | 73 |
| 31 | 94 | 67 | 73 |
| 32 | 97 | 69 | 73 |
| 33 | 100 | 71 | 73 |
| 34 | 103 | 73 | 73 |
| 35 | 106 | 75 | 73 |
| 36 | 109 | 77 | 73 |

For this example, it can be seen that the individual addressing mode (i.e., the second mode) is most efficient when the number of electrodes being reconfigured is less than five, the bitmap addressing mode (i.e., the third mode) is most efficient when the number of electrodes being reconfigured is between five and thirty-three, and the full reconfiguration mode (i.e., the first mode) is most efficient when the number of electrodes being reconfigured is greater than thirty-five.

In certain embodiments, these rules may be implemented in hardware or software for the implantable stimulating device.

Figure 2:
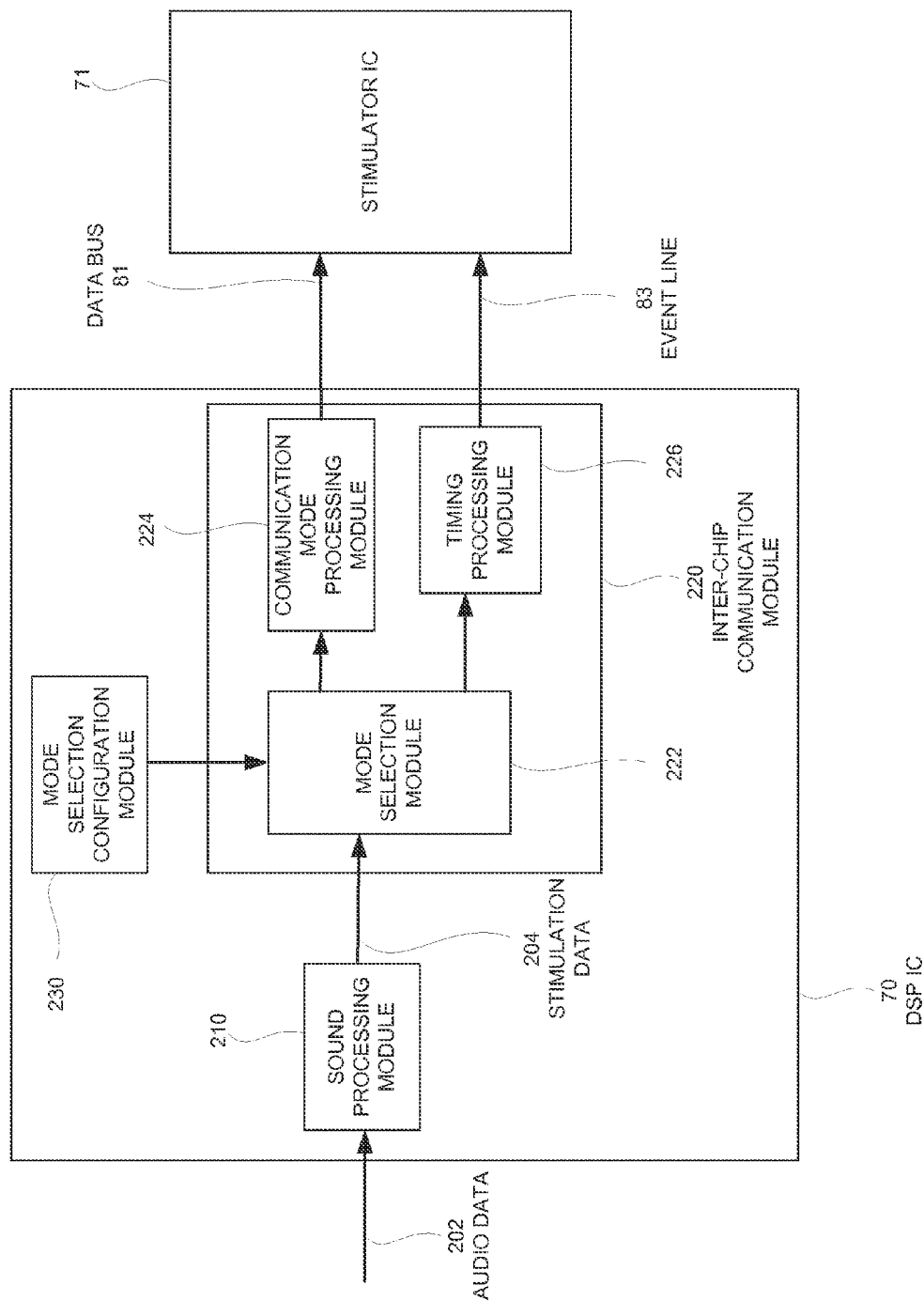
FIG. 2 is a functional block diagram of portions of an implantable system in accordance with embodiments of the present invention.
Figure 3:
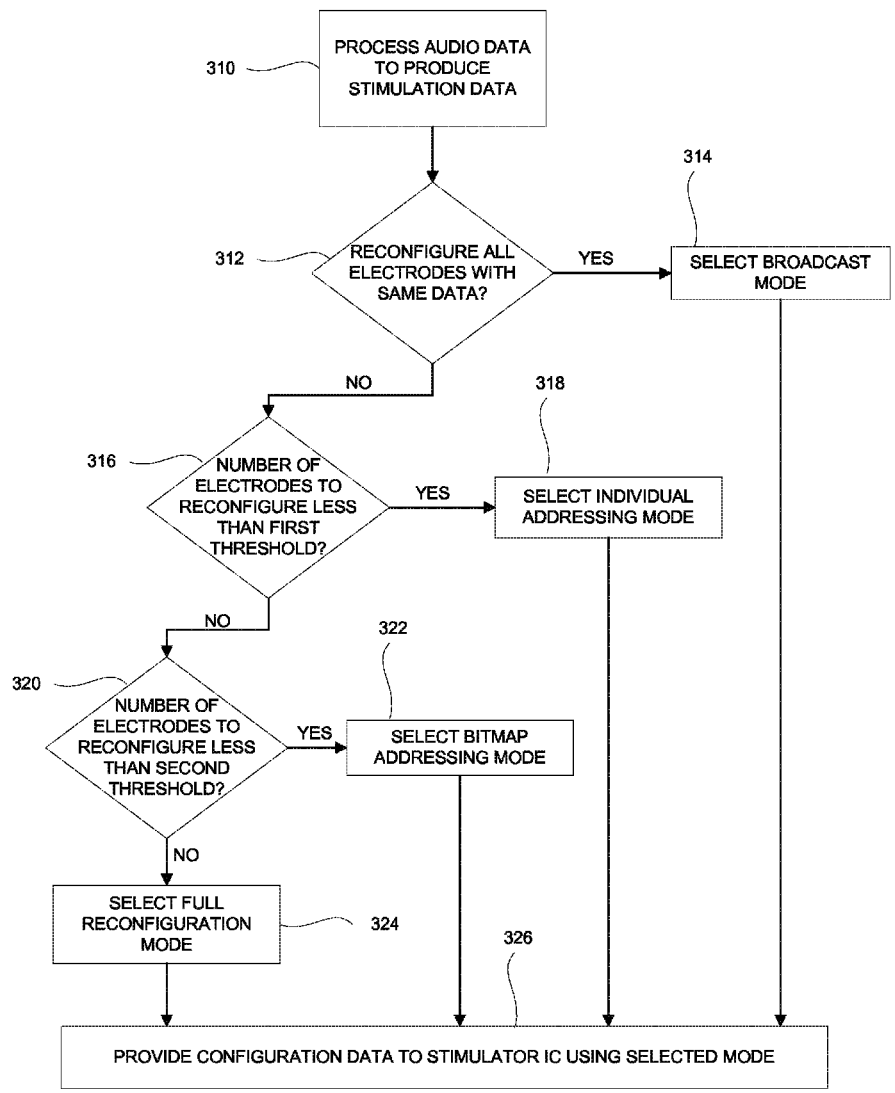
FIG. 3 is a flow chart illustrating a process for communicating configuration data from a signal processor IC to a stimulator IC in accordance with embodiments of the present invention.

FIG. 2 is a functional block diagram of portions of implantable system 50 in accordance with embodiments of the present invention. As shown, the implantable system 50 of FIG. 2 includes DSP IC 70 and stimulator IC 71. FIG. 3 is a flow chart illustrating a process for communicating configuration data from a signal processor IC to a stimulator IC in accordance with embodiments of the present invention. The exemplary process of FIG. 3 will be described below with reference to FIG. 2.

At block 310 of FIG. 3, audio data is processed to produce stimulation data. In certain embodiments, audio data 202 is received from outside of DSP IC 70. For example, audio data 202 may be received from sound processor 20 via wireless link 61 illustrated in FIG. 1. In the embodiment illustrated in FIG. 2, audio data 202 is provided to a sound processing module 210 of DSP IC 70. Sound processing module 210 processes audio data 202 to generate stimulation data 204. In some embodiments, sound processing module 210 includes one or more digital signal processors that utilize digital signal processing software to process audio data 202 to generate stimulation data 204. In certain embodiments, sound processing module 210 may be implemented in hardware, software, firmware, or a combination thereof. As shown in FIG. 2, sound processing module 210 provides stimulation data 204 to mode selection module 222 of inter-chip communication module 220 of DSP IC 70. In certain embodiments, mode selection module 222 selects, based on stimulation data 204, a communication mode for providing stimulation instructions to stimulator IC 71 via a communication interface 80. In such embodiments, the stimulation instructions are based on stimulation data 204. An exemplary process by which mode selection module 222 may select the communication mode, in some embodiments, is described below with reference to the flowchart of FIG. 3.

In certain embodiments, at block 312 of FIG. 3, mode selection module 222 determines whether all electrodes are to be reconfigured with the same configuration data for a stimulation event. If all of the electrodes are to be reconfigured with the same configuration data, then mode selection module 222 selects the broadcast mode at block 314. If not, then mode selection module 222 proceeds to block 316. At block 316, mode selection module 222 determines whether the number of electrodes to be reconfigured for a stimulation event is less than a first threshold number of electrodes. If so, then mode selection module 222 selects the individual addressing mode at block 318. If not, then mode selection module 222 proceeds to block 320. In alternative embodiments, mode selection module 222 may determine, at block 316, whether the number of electrodes to be reconfigured for a stimulation event is less or equal to the first threshold number of electrodes.

At block 320, mode selection module 222 determines whether the number of electrodes to be reconfigured for a stimulation event is less than a second threshold number of electrodes. If so, mode selection module 222 selects the bitmap addressing mode at block 322. If not, mode selection module 222 selects the full reconfiguration mode at block 324. In alternative embodiments, mode selection module 222 may determine, at block 320, whether the number of electrodes to be reconfigured for a stimulation event is less than or equal to the second threshold number of electrodes. In certain embodiments, mode selection module 222 is implemented in hardware. In such embodiments, the hardware is configured to make the determinations described above in order to select the communication mode based on the number of electrodes being reconfigured for one stimulation event. In the embodiment illustrated in FIG. 2, mode selection configuration module 230 sets the first and second thresholds used by mode selection module 222 to select the communication mode. In embodiments in which mode selection module 222 is implemented in hardware, mode selection configuration module 230 may program (or configure) mode selection module 222 in order to set the appropriate threshold levels. In certain embodiments, the thresholds are set by mode selection configuration module 230 at the start-up of the system and remain the same during the subsequent operation of the system. In alternative embodiments, mode selection module 222 and mode selection configuration module 230 may be implemented in hardware, software, firmware, or a combination thereof.

At block 326 of FIG. 3, DSP IC 70 provides configuration data to stimulator IC 71 using the selected mode. In certain embodiments, a communication mode processing module 224 of inter-chip communication module 220 implements the communication mode selected by the mode selection module 222. In some embodiments, mode selection module 222 provides stimulation data 204 and an indication of the selected mode to communication mode processing module 224. In alternative embodiments, mode selection module 222 may provide communication mode processing module 224 with only a portion of stimulation data 204, or with data generated from stimulation data 204. Communication mode processing module 224 formats the stimulation data in accordance with the selected communication mode and provides stimulation instructions, including the electrode configuration data, to stimulator IC 71 via data bus 81. Depending on the selected communication mode, communication mode processing module 224 may also provide electrode address data or an address bitmap on data bus 81 along with the configuration data as part of the stimulation instructions. In certain embodiments, DSP IC 70 may provide configuration data to stimulator IC 71 using the broadcast mode to configure all of the electrodes with the same value(s) for one or more parameters prior to providing configuration data to stimulator IC 71 using one of the other modes. In such embodiments, DSP IC 70 may use the broadcast mode to set each electrode with the same magnitude (which may be referred to herein as "resetting" all of the electrodes) prior to providing configuration data to stimulator IC 71 using one of the other modes, such as the individual addressing mode or the bitmap addressing mode. Additionally, in such embodiments, DSP IC 70 may reset all of the electrodes using the broadcast mode either before or after selecting a communication mode Also at block 326 of FIG. 3, DSP IC 70 provides timing data to stimulator IC 71 as part of the stimulation instructions provided to stimulator IC 71. In the embodiment illustrated in FIG. 2, mode selection module 222 provides timing processing module 226 with stimulation data 204, a portion of stimulation data 204, or data generated from stimulation data 204. Timing processing module 226 uses the received data to generate timing information that corresponds to the configuration data output by communication mode processing module 224. In certain embodiments, timing processing module 226 provides the timing information to stimulator IC 71 via event line 83. In certain embodiments, the timing information is provided to stimulator IC 71 after a delay relative to when the configuration data is output. In some embodiments, the length of the delay may be fixed. In other embodiments, the length of the delay may be greater than or equal to a pre-set minimum delay. In certain embodiments, the timing information indicates when to reconfigure the electrodes with the configuration data provided to stimulator IC 71. In such embodiments, the configuration data may indicate the magnitude of stimulation applied via one or more electrodes and the timing information indicates when that magnitude of stimulation is to be applied. In such embodiments, the stimulator IC 71 uses the configuration data and the timing information of the stimulation instructions to apply the specified electrical stimulation. In some embodiments, mode selection module 222, communication mode processing module 224 and timing processing module 226 are all implemented in hardware. In alternative embodiments, modules 222, 224 and 226 may be implemented in hardware, software, firmware, or a combination thereof. In certain embodiments, after providing configuration data and/or timing data to stimulator IC 71 at block 326, the process may begin again at block 310 with new audio data.

In some embodiments, communication interface 80 may be used for reading from and writing to any register in stimulator IC 71. Communication interface 80 is a bi-directional logical channel that uses the forward channel to communicate to stimulator IC 71 and the back channel to retrieve data from stimulator IC 71. It will be understood from the previous discussion that, in certain embodiments, the forward channel includes an n-bit parallel bus in which multiple lines transfer data simultaneously.

Figures 15A, 15B:
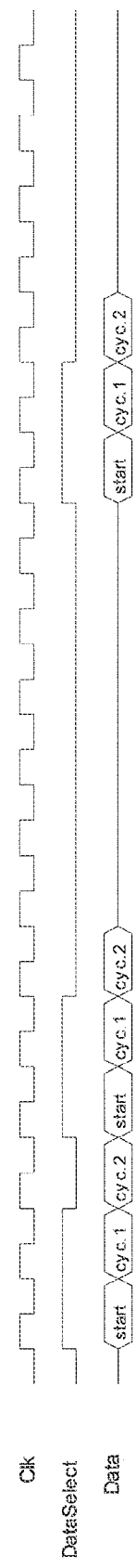
FIG. 15A illustrates a write message frame for writing data to the stimulator IC in accordance with embodiments of the present invention.
FIG. 15B is a timing diagram for several signals during a write operation to the stimulator IC in accordance with embodiments of the present invention.

FIG. 15A illustrates a write message frame for writing data to the stimulator IC in accordance with embodiments of the present invention. In certain embodiments, to write data to stimulator IC 71, DSP IC 70 generates a message frame as depicted in FIG. 15A. The frame starts with a read/write selection bit (bit 6 of the start cycle), which, in the embodiment of FIG. 15A, is a '0' for a write cycle. In such embodiments, a '1' indicates a read cycle. In other embodiments, a '1' may indicate a write cycle and a '0' may indicate a read cycle. Bit 5 is set to 0, and bits 4 through 2 are unused. FIG. 15B is a timing diagram illustrating the clock signal, the data select signal and data on the data lines for a write operation in accordance with embodiments of the present invention.

FIG. 16A illustrates a read message frame for reading data from the stimulator IC in accordance with embodiments of the present invention. To read data from stimulator IC 71, DSP IC 70 generates a message frame, as depicted in FIG. 16A, which is similar to the message frame of FIG. 15A for a write operation. Compared to the write message frame of the writing operation, in the message frame of the reading operation the read/write-bit is set to '1' and the frame does not contain a data portion. Also, the CRC bit is fixed to '0'. As noted above, in other embodiments, a '0' could indicate a read cycle, while a '1' indicates a write cycle. FIG. 16B is a timing diagram illustrating the clock signal, the data select signal, and data on the data lines and back channel for a read operation in accordance with embodiments of the present invention.

It will be appreciated that many alternative IC communication approaches are possible, which incorporate the inventive approach to data modes described above in relation to embodiments of the present invention. In particular, while four electrode reconfiguration modes are discussed herein, some embodiments may utilize more or fewer modes.

While various embodiments have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents. The present embodiments are, therefore, to be considered in all respects as illustrative and not restrictive. Additionally, it will be appreciated that any features, components, elements, etc., described above in relation to different exemplary embodiments may be implemented together.

What is claimed is:

1. A device comprising:
    a first integrated circuit (IC);
    a second IC configured to provide instructions to the first IC based on received data; and
    a communication interface between the first and second ICs, wherein the second IC is configured to select, based on the received data, one of a plurality of different communication modes for providing the instructions to the first IC via the communication interface, wherein each mode is defined by a quantity of address data and a quantity of configuration data used to provide the instructions to the first IC.

2. The device of claim 1, wherein the second IC is further configured to select one of the modes to reduce the power consumption of the communication interface.

3. The device of claim 1, further comprising:
a plurality of addressable components.

4. The device of claim 3, wherein the plurality of modes includes a mode in which the address of and configuration data for each addressable component of a subset of the plurality of addressable components is provided over the communication interface.

5. The device of claim 4, wherein the subset includes fewer than all of the plurality of addressable components.

6. The device of claim 3, wherein the plurality of modes includes a mode in which a bitmap, specifying a subset of the addressable components, and configuration data for each of the addressable components specified in the bitmap is provided over the communication interface, wherein the subset includes all or fewer than all of the electrodes.

7. The device of claim 3, wherein the plurality of modes includes a mode in which no address data is used to provide the instructions to the first IC.

8. The device of claim 3, wherein the second IC is further configured to generate stimulation data from the received data and to select one of the plurality of communication modes based on the number of the addressable components to be reconfigured in response to the stimulation data.

9. The device of claim 8, wherein the second IC comprises:
a mode selection module configured to select the one of the plurality of communication modes.

10. The device of claim 3, wherein the plurality of addressable components are a plurality of electrodes, the instructions are stimulation instructions, the first IC is configured to provide electrical stimulation to a plurality of electrodes, and the second IC is configured to generate the stimulation instructions from the received data.

11. The device of claim 1, wherein the highest voltage utilized by the second IC is significantly lower than the highest voltage utilized by the first IC.

12. The device of claim 11, wherein the highest voltage utilized by the first IC is at least twice as high as the highest voltage utilized by the second IC.

13. The device of claim 1, wherein the highest voltage utilized by the first IC is at least five volts.

14. The device of claim 1, wherein the first IC is a high-voltage IC and the second IC is a low-voltage IC.

15. The device of claim 1, wherein the communication interface comprises a data bus of parallel data lines.

16. The device of claim 1, wherein the second IC is a mixed signal IC and wherein the first IC is a digital IC.

17. A device comprising:
a plurality of addressable components;
a first integrated circuit (IC) configured to selectively drive one or more of the addressable components based on reconfigurable driving instructions;
a second IC configured to:
provide a set of reconfigured driving instructions for one or more of the addressable components to the first IC using one of a plurality of different communication modes; and
select amongst the plurality of different communication modes based on how many of the addressable components will receive reconfigured driving instructions.

18. The device of claim 17, wherein the plurality of different communication modes includes at least one of:
a first communication mode in which all of the addressable components will receive reconfigured driving instructions, respectively; and
a second communication mode in which at least some but fewer than all of the addressable components will receive reconfigured driving instructions, respectively.

19. The device of claim 18, wherein the first communication mode includes at least one of the following variants:
a first variant in which at least two of the of the addressable components will receive different reconfigured driving instructions; and
a second variant in which all of the addressable components will receive the same reconfigured driving instruction.

20. The device of claim 18, wherein the second communication mode includes at least one of the following variants:
a first variant in which the set of reconfigured driving instructions includes discrete driving instructions, each discrete driving instruction including a discrete unit of configuration data and a discrete unit of address data; and
a second variant in which the set of reconfigured driving instructions includes:
a bit map representing the addresses of the addressable components that will receive reconfigured driving instructions; and
a set of discrete units of configuration data.

21. The device of claim 20, wherein the second IC is further configured, for a given set of reconfigured driving instructions, to select between the first and second variants of the second communication mode as follows:
when the sum of bits in the discrete units of address data according to the first variant exceeds the number of bits in the bitmap according to second variant, the second IC is further configured to select the second variant.

22. The device of claim 17, wherein:
second IC is a stimulator IC;
the plurality of addressable components is a plurality of electrodes implantable in a recipient; and
the reconfigurable driving instructions are stimulation instructions.

23. A device comprising:
a plurality of addressable components;
a first integrated circuit (IC) configured to selectively drive one or more of the addressable components based on reconfigurable driving instructions;
a second IC configured to:
provide a set of data representing reconfigured driving instructions for one or more of the addressable components to the first IC using one of a plurality of different communication modes; and
select amongst the plurality of different communication modes based on which mode requires the least amount of power to communicate the quantity of data in the set.

24. The device of claim 23, wherein the plurality of different communication modes includes at least one of:
a first communication mode requiring a first amount of power consumable by the second IC when the second IC communicates reconfigured driving instructions to all of the addressable components, respectively; and
a second communication mode requiring a second amount of power consumable by the second IC when the second IC communicates reconfigured driving instructions to at least some but fewer than all of the addressable components, respectively.

25. The device of claim 24, wherein the first communication mode includes at least one of the following variants:
   a first variant in which the first amount of power corresponds to a first quantity of power consumable by the second IC when the second IC communicates different reconfigured driving instructions to at least two of the of the addressable components; and
   a second variant in which the first amount of power corresponds to a second quantity of power consumable by the second IC when the second IC communicates the same reconfigured driving instruction to all of the addressable components.

26. The device of claim 24, wherein the second communication mode includes at least one of the following variants:
   a first variant in which the second amount of power corresponds to a first quantity of power consumable by the second IC when the set of reconfigured driving instructions communicated by the second IC includes discrete driving instructions, each discrete driving instruction including a discrete unit of configuration data and a discrete unit of address data; and
   a second variant in which the second amount of power corresponds to a second quantity of power consumable by the second IC when the set of reconfigured driving instructions communicated by the second IC includes:
      a bit map representing the addresses of the addressable components that will receive reconfigured driving instructions; and
      a set of discrete units of configuration data.

27. The device of claim 26, wherein:
   the second IC is further configured, for a given set of reconfigured driving instructions communicable according to the second communication mode, to represent:
      the first quantity of power as the sum of bits in the discrete units of address data according to the first variant; and
      the second quantity of power as the number of bits in the bitmap according to second variant; and
   the second IC is further configured to select between the first and second variants of the second communication mode when the first quantity exceeds the second quantity.

28. The device of claim 23, wherein:
   second IC is a stimulator IC;
   the plurality of addressable components is a plurality of electrodes implantable in a recipient; and
   the reconfigurable driving instructions are stimulation instructions.

* * * * *